United States Patent [19]
Cox

[11] 3,978,877
[45] Sept. 7, 1976

[54] METHOD AND APPARATUS FOR MONITORING AND CONTROLLING THE COMPOSITION OF FLAMMABLE GAS MIXTURES

[75] Inventor: Bruce M. Cox, Duncan, Okla.

[73] Assignee: Halliburton Company, Duncan, Okla.

[22] Filed: June 4, 1975

[21] Appl. No.: 583,735

Related U.S. Application Data

[62] Division of Ser. No. 502,389, Sept. 3, 1974, Pat. No. 3,913,600.

[52] U.S. Cl. ........................................ 137/90; 73/35
[51] Int. Cl.² .......................................... G05D 11/00
[58] Field of Search ................ 73/26, 35, 36; 137/6, 137/90

[56] References Cited
UNITED STATES PATENTS

| | | | |
|---|---|---|---|
| 2,072,384 | 3/1937 | Schmidt | 137/90 |
| 2,737,965 | 3/1956 | Newman | 137/90 |
| 2,866,602 | 12/1958 | Dailey, Jr. et al. | 137/90 |
| 3,293,905 | 12/1966 | Ratway et al. | 73/36 |
| 3,768,313 | 10/1973 | Johansson et al. | 73/26 |

Primary Examiner—Martin P. Schwadron
Assistant Examiner—G. L. Walton
Attorney, Agent, or Firm—John H. Tregoning; Bruce E. Burdick

[57] ABSTRACT

An improved apparatus for monitoring and controlling the composition of a flammable gas mixture to prevent accumulation of explosive gas mixtures in a substantially closed container. The apparatus includes a combustion chamber through which a sample stream of gas mixture is propelled. In operating the apparatus, the mixture within the combustion chamber is subjected to a series of high voltage ignition charges by means of an automotive spark plug which receives ignition charges from a conventional automotive capacitor discharge ignition system power unit and automotive ignition coil with the ignition charges being triggered by an electrically powered oscillator at a frequency preferably between 10 and 20 Hz. The electrical components and combustion chamber are housed within an explosion proof housing. A temperature responsive switch within the combustion chamber causes the actuation of solenoid operated pneumatic valves to provide continuing visual indication of the status of the system and provide injection of non-combustion-supporting gas into the closed container to prevent accumulation of explosive mixtures therein.

9 Claims, 4 Drawing Figures

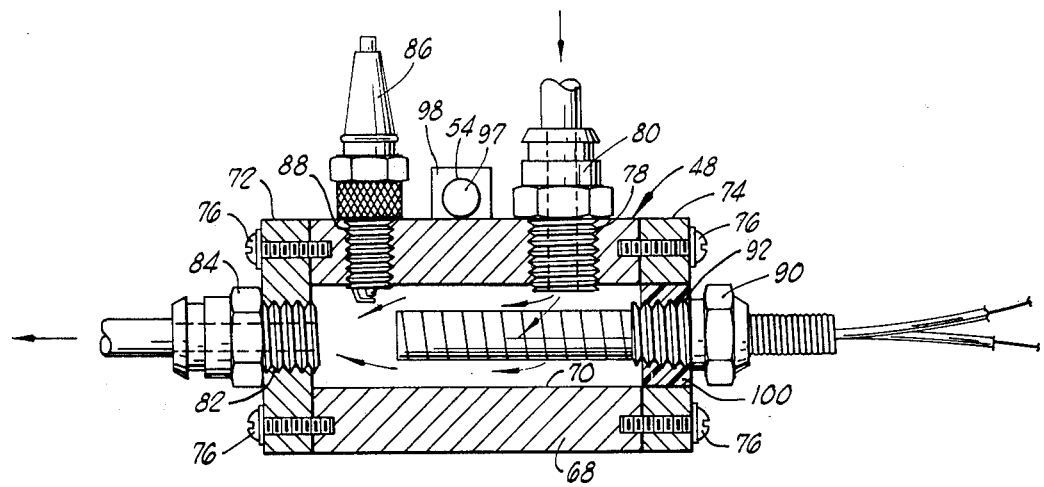
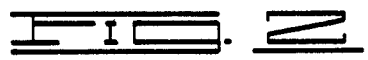
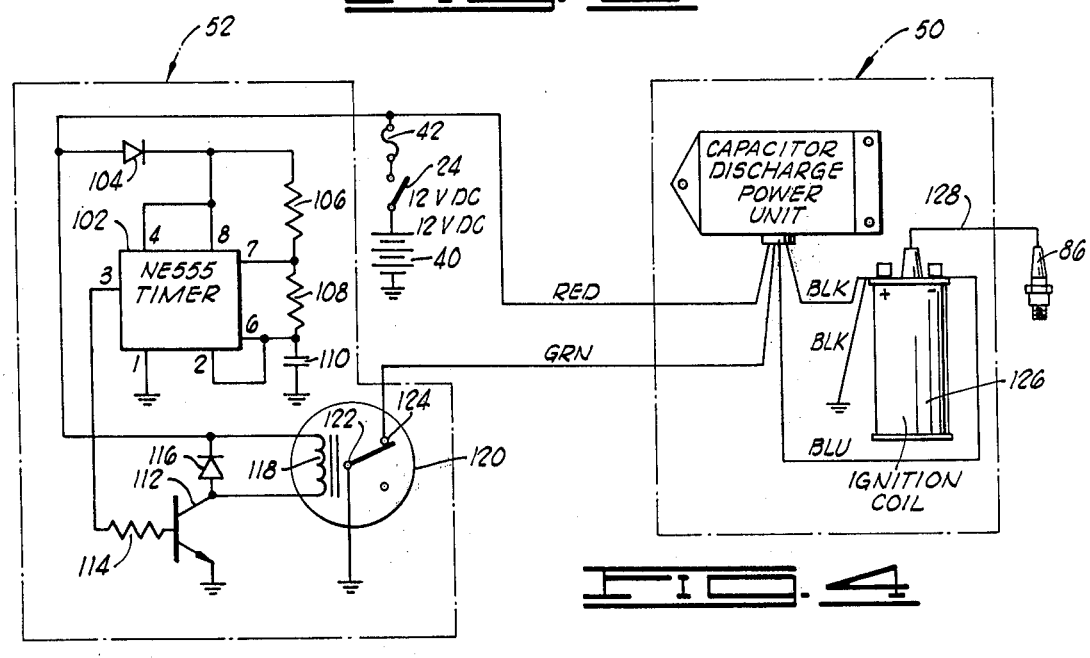
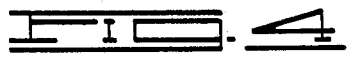
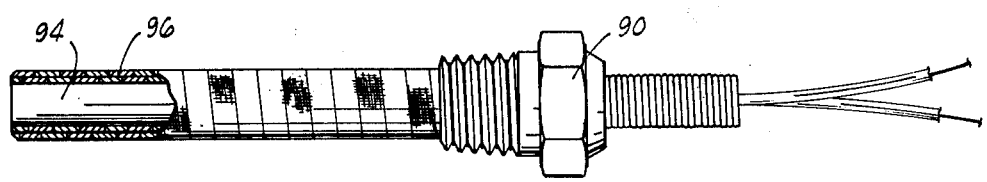
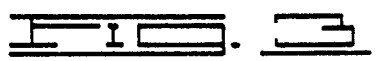

METHOD AND APPARATUS FOR MONITORING AND CONTROLLING THE COMPOSITION OF FLAMMABLE GAS MIXTURES

This is a division of application Ser. No. 502,389, filed Sept. 3, 1974 now U.S. Pat. No. 3,913,600.

BACKGROUND OF THE INVENTION

1. Field of the Invention

The present invention relates generally to improvements in detectors of flammable gas mixtures, and more particularly, but not by way of limitation, to method and apparatus for monitoring and controlling the composition of potentially explosive flammable gas mixtures.

2. Description of the Prior Art

The prior art contains a number of teachings of gas sensors which rely on a catalytic reaction, gas absorption or spectrum analysis to identify the presence of a flammable or explosive gas mixture. Such prior art devices generally require advance knowledge of the composition of the gas under test and advance calibration in order for the devices to sense the presence of a particular gas or gas mixture. When so calibrated, these devices can only be relied on to indicate the presence of the gas or gas mixture for which the calibration was made. Those devices which employ platinum wire catalysts have been found to be unsatisfactory when employed with gas mixtures which include hydrocarbons or carbon dioxide which destroy the effectiveness of the catalysts.

SUMMARY OF THE INVENTION

The present invention contemplates an apparatus for use with a source of electric current for monitoring and controlling the composition of gaseous mixtures in a substantially closed container to prevent the accumulation of explosive gas mixtures therein. The apparatus includes a combustion chamber having an inlet and an outlet, conduit means communicating between the closed container and the inlet of the combustion chamber for conveying a sample stream of gas mixture from the container to the combustion chamber, and pump means communicating with the conduit means for propelling the sample gas mixture stream through the conduit means to the combustion chamber. The apparatus further includes ignition generation means connected with the source of electric current and communicating with the interior of the combustion chamber for providing periodic ignition energy to the interior of the combustion chamber to ignite any explosive gas mixture therein. Temperature responsive switch means communicating with the interior of the combustion chamber is provided in the apparatus and is connected to the source of electric current for blocking passage of electric current therethrough in response to temperatures sensed in the combustion chamber less than a predetermined value and, alternately, passing electric current therethrough in response to temperatures sensed in the combustion chamber greater than the predetermined value. The apparatus further includes means electrically connected to the temperature responsive switch means and responsive thereto for introducing non-combustion-supporting gas into the closed container upon the sensing of a temperature within the combustion chamber greater than the predetermined value.

It is an object of the present invention to provide improved method and apparatus for continuously testing and adjusting the composition of a gas mixture in a zone under test to prevent the accumulation of an explosive gas mixture in the zone.

Another object of the present invention is to provide an improved apparatus for monitoring and controlling the composition of gaseous mixtures of unknown components in a test zone to prevent the accumulation of an explosive gas mixture therein.

A further object of the present invention is to provide an apparatus for used in monitoring and controlling the composition of gaseous mixtures of unknown components in a test zone to prevent the accumulation of an explosive gas mixture therein.

A further object of the present invention is to provide an apparatus for use in monitoring and controlling the composition of gaseous mixtures which is economical to construct and simple, safe and economical to operate.

Other objects and advantages of the invention will be evident from the following detailed description when read in conjunction with the accompanying drawings.

BRIEF DESCRIPTION OF THE DRAWINGS

FIG. 2 is an enlarged cross-sectional view of the combustion chamber of the present invention.

FIG. 3 is an enlarged elevation view of the temperature responsive switch of the present invention with portions broken away to more clearly illustrate the construction details thereof.

FIG. 4 is an electrical circuit diagram illustrating the ignition system of the present invention.

DESCRIPTION OF THE PREFERRED EMBODIMENT

Figure 1:
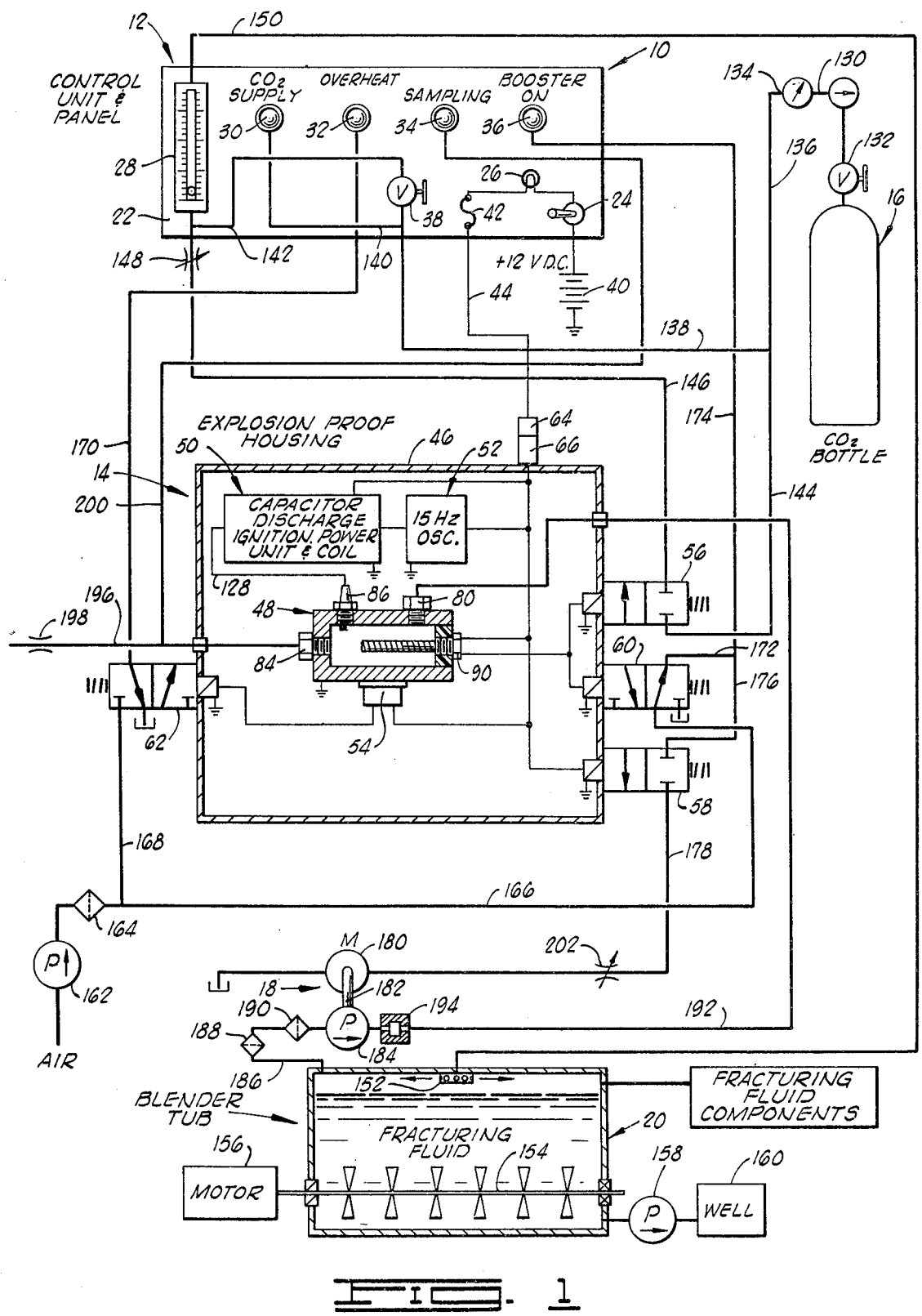
FIG. 1 is a diagrammatical illustration of the apparatus of the present invention.

Referring now to the drawings, the apparatus of the present invention is generally designated by the reference character 10. The apparatus 10 generally includes a control unit and panel assembly 12, a flammable gas tester and controller assembly 14, a non-combustion-supporting gas container assembly 16, and a gas sample pump assembly 18. The apparatus 10 is illustrated in FIG. 1 operating in conjunction with a closed blender tub assembly 20 which is used for mixing highly flammable oil well fracturing fluids therein.

The control unit and panel assembly 12 includes a control panel 22 upon which is mounted on on-off toggle switch 24 for activating and deactivating the apparatus 10. An indicator light 26 is included on the panel 22 to provide visual indication when the apparatus 10 is turned on.

The panel 22 also includes a gas flow meter 28 to provide visual indication of the rate of gas flow therethrough. Four gas pressure-actuated visual indicators 30, 32, 34 and 36 are provided on the control panel 22. The indicator 30 alternately provides green and red visual indicators, the green visual indicator meaning that non-combustion-supporting gas, preferably $CO_2$, is available to the apparatus 10 for use in controlling the composition of the flammable gas mixtures. A red indication on the indicator 30 shows that there is an insufficient supply of $CO_2$ available for use with the apparatus 10.

The visual indicator 32 provides a visual red indicator in the event of overheating of the flammable gas tester and control assembly 14 while ordinarily providing a black indicator under normal operating circumstances.

The visual indicator 34 provides a green visual indication when the gas sample pump assembly 18 is propelling a gas sample stream through the flammable gas tester and control assembly 14 and, alternately, provides a red indication when the apparatus 10 is not performing a sampling operation.

The visual indicator 36 provides a black visual indicator under normal circumstances and, alternately, provides a red visual indication when the apparatus 10 is providing non-combustion-supporting gas, preferably $CO_2$, to the container in which the gas is under test is housed when the gas under test is shown to be a flammable mixture.

The control panel 22 also carries an adjustable throttle valve shown schematically at 38. One side of the switch 24 is electrically connected to a source of electrical current such as a 12 volt D.C. storage battery 40. The other side of the switch 24 is electrically connected to the indicator light 26 which is in turn connected to one side of a suitable fuse 42. The other side of the fuse 42 is electrically connected to a suitable shielded electriical cable 44 to provide a conduit for electrical current from the control unit and panel assembly 12 to the flammable gas tester and controller assembly 14.

The flammable gas tester and controller assembly 14 includes a conventional explosion proof housing 46 in which is located a combustion chamber assembly 48, a capacitor discharge power unit and ignition coil assembly 50, an electronic ignition trigger oscillator assembly 52, and a temperature responsive electrical switch 54 positioned adjacent to the exterior of the combustion chamber assembly 48. Mounted on the explosion proof housing 46 are two 2-way, normally closed, solenoid valves 56 and 58, and two 3-way multi-purpose solenoid valves 60 and 62. The conductor of the electrical cable 44 enters the explosion proof housing 46 via a suitable cord connector 64 and explosion proof sealing fitting 66. The solenoid valves 56, 58, 60 and 62 and the connector and fitting 64 and 66 are of commercially available conventional construction. The electrical interconnections of the various elements of the flammable gas tester and controller assembly 14 are preferably completely confined within the explosion proof housing 46.

The combustion chamber assembly 48 includes a body member 68 with a longitudinal passageway 70 extending therethrough. The longitudinal passageway 70 is closed at each end thereof by means of end plates 72 and 74 suitably secured to the body member 68 by means of threaded screws 76. An inlet port 78 is formed in the body member 68 with internal threads formed therein. An explosion proof gas inlet fitting or flame arrestor 80 is threadedly secured in the inlet port 78 to provide means for introducing a gas sample into the combustion chamber assembly 48. The gas inlet fitting 80 is preferably of conventional construction wherein the passageway therethrough is substantially filled with a bundle of fine metallic wire to prevent the propagation of flame from the interior of the combustion chamber assembly 48 through the gas inlet fitting 80.

An outlet port 82 is formed in the end plate 72 and includes internal threads formed therein. An explosion proof gas outlet fitting or flame arrestor 84 is threadedly secured within the outlet port 82. The construction of the gas outlet fitting 84 is preferably identical to that of the gas inlet fitting 80. The gas outlet fitting 84 provides means for exhausting the gas mixture sample stream from the combustion chamber assembly 48 during operation.

A conventional automotive spark plug 86 is threadedly secured in an internally threaded aperture 88 formed in the body member 68 adjacent to the outlet port 82.

A temperature responsive, snap action electrical switch 90 is threadedly secured within an internally threadedly aperture 92. The temperature sensitive portion of the temperature responsive switch 90 extends through the longitudinal passageways 70 of the body member 68 to a point adjacent to the cathode and anode of the spark plug 86. The temperature responsive switch 90 is preferably a modified version of a Series 67100 temperature controller manufactured by Fenwal Incorporated, Ashland, Massachusetts. As illustrated in FIG. 3, the temperature responsive switch has been modified by winding successive layers of braided copper wire material known as "solder wick" around the stainless steel temperature sensitive tip of the switch and securing the "solder wick" to the stainless steel tip by means of silver solder. The silver soldered braided copper material secured to the stainless steel tip 94 of the switch 90 is designated by the reference character 96 in FIG. 3. The addition of the braided copper material to the commercially available temperature responsive switch 90 provides little change in the response of the switch to increases in temperature within the combustion chamber while at the same time reducing the speed with which heat is lost from the temperature responsive portion of the switch 90 when the temperature within the combustion chamber falls below the predetermined actuation temperature of the switch. This time delay characteristic of the modified switch 90 provides for increased stability of operation of the apparatus 10 as will become more apparent as the invention is further described. It should be noted that the switch 90 is preferably calibrated such that it closes on a sensed temperature rise to 300°F.

The temperature responsive switch 54 is shown mounted with the temperature responsive portion thereof 97 positioned adjacent to the exterior of the combustion chamber assembly 48. The switch 54 is preferably substantially identical to the commercially available switch utilized in the switch 90 described above but without the time delay modifications employed in the switch 90. The switch 54 may be suitably threadedly secured in an internally threaded bracket 98 mounted on the body member 68 of the combustion chamber assembly 48.

It should further be noted that the end plate 74 may be advantageously formed of a suitable metallic material with the annular portion 100 surrounding the internally threaded aperture 92 being formed of suitable synthetic epoxy resin material having thermal conductivity properties substantially lower than the thermal conductivity of the metallic portion of the end plate 74 to provide a degree of thermal insulation between the temperature responsive switch 90 and the metallic portion of the end plate 74. This structural arrangement provides increased sensitivity of the temperature responsive switch 90 to the temperature of the gases within the combustion chamber 48 while minimizing the effect of heat which might otherwise be conducted from the end plate 74 to the switch 90 resulting in reduced reaction time in the opening of the switch 90 when a flammable gas mixture is no longer present within the combustion chamber assembly 48.

The electronic ignition trigger oscillator assembly 52 is schematically illustrated in FIG. 4. The oscillator 52 comprises an NE 555 timer manufactured by Signetics and designated by the reference character 102. The positive terminal of the storage battery 40 is connected to pins 4 and 8 of the timer 102 via the on-off toggle switch 24, fuse 42 and a diode 104 which provides reverse polarity protection. Pin 7 of timer 102 is connected to the cathode of the diode 104 via a resistor 106. Pins 2 and 6 of the timer 102 are connected with pin 7 via a resistor 108 and are further connected to ground via a capacitor 110. Pin 1 is connected directly to ground. Pin 3 of the timer 102 is connected to the base of an NPN transistor 112 via a resistor 114. The emitter of the transistor 112 is grounded while the collector is connected to the anode of a diode 116. The cathode of the diode 116 is connected to the anode of the diode 104 and one end of the coil 118 of a miniature electromagnetic relay 120 while the other end of the coil 118 is connected to the anode of the diode 116. One terminal 122 of the relay 120 is connected directly to ground while another terminal 124 is connected to the capacitor discharge ignition power unit 50 as will be described in detail hereinafter.

The resistors 106 and 108 and the capacitor 110 are selected to provide a frequency of oscillation of approximately 15 Hz. The transistor 112 is preferably a 2N2895 type NPN transistor. The miniature electromagnetic relay is preferably a number 712D transistor case relay manufactured by Teledyne.

The capacitor discharge ignition power unit of the capacitor discharge ignition power unit and coil assembly 50 is commercially available from Motorola and is identified by the number 6CB2011. The red wire from the capacitor discharge ignition power unit is connected to the anode of the diode 104. The green wire of the power unit is connected to the terminal 124 of the relay 120 as mentioned above. The blue wire from the power unit is connected to the negative terminal of a conventional automotive ignition coil 126 of the capacitor ignition power unit and coil assembly 50. The black wire from the ignition power unit is connected to the positive terminal of the ignition coil 126 which terminal is in turn connected directly to ground. The high tension lead 128 from the ignition coil 126 is connected to the spark plug 86 of the combustion chamber assembly 48.

Referring again to FIG. 1, it will be seen that the gas container assembly 16, preferably containing compressed carbon dioxide, is connected to a suitable pressure regulator 130 via a shut off valve 132. The pressure regulator 130 is of conventional design and is preferably adjusted to provide a substantially constant output of $CO_2$ at 100 p.s.i. The outlet 134 of the pressure regulator 130 is connected by means of suitable conduits 136 and 138 to the inlet of the adjustable throttle valve 38 of the control unit and panel assembly 12. A conduit 140 connects the inlet of the valve 38 with the visual indicator 30. The outlet of the valve 38 is connected by conduit 142 to the inlet of the gas flow meter 28.

The outlet 134 of the pressure regulator 130 is also connected by conduits 136 and 144 to the inlet of the solenoid valve 56. The outlet of solenoid valve 56 is connected by means of conduit 146 and an adjustable throttle or needle valve 148 to the inlet of the gas flow meter 28. The valve 148 is of conventional design and, under certain design circumstances, may be replaced by a fixed orifice.

The outlet of the gas flow meter 28 is connected by means of a suitable conduit 150 to a gas distribution nozzle 152 located within the upper portion of the closed blender tub assembly 20 above the fracturing fluid being blended therein. The nozzle 152 provides $CO_2$ or other suitable non-combustion-supporting gas to the interior of the blender tub assembly 20 under the control of the apparatus 10 to prevent the accumulation of explosive gas mixtures within the tub above the fracturing fluid.

The closed blender tub assembly 20 typically includes a transversely journaled agitator 154 extending through the interior of the tub and driven by a suitable motor 156. Fracturing fluid is typically pumped from the tub through suitable conduits by means of a high pressure fracturing pump 158 which forces the fracturing fluid into the bore of a well 160 for fracturing formations penetrated by the bore of the well.

A suitable air pump 162 provides air under pressure through a filter 164 to the inlet of solenoid valve 60 via conduit 166, and to the inlet of solenoid valve 62 via conduit 168. The outlet of solenoid valve 62 is connected by conduit 170 to the visual indicator 32 of the control unit and panel assembly 12. The outlet of solenoid valve 60 is connected via conduits 172 and 174 to the visual indicator 36 of the control unit and panel assembly 12, and is connected by conduits 172 and 176 to the inlet of solenoid valve 58. The outlet of solenoid valve 58 is connected via conduit 178 to the inlet of a suitable air motor 180 which in turn provides driving force via a drive shaft 182 to an air pump 184.

The inlet of the pump 184 communicates with the interior of the blender tub assembly 20 above the level of the fracturing fluid contained therein via a conduit 186 and a pair of five micron filters 188 and 190 interposed in the conduit 186. The outlet of the air pump 184 communicates with one end of a conduit 192 via an explosion proof gas outlet fitting or flame arrestor 194 of a construction substantially identical to that described above for the explosion proof fittings 80 and 84. The opposite end of the conduit 192 extends through the explosion proof housing 46 and communicates with the explosion proof gas inlet fitting 80 of the combustion chamber assembly 48. It will be understood that the conduit 192 is provided with a suitable explosion proof connection with the housing 46 at its point of entrance therethrough. A conduit 196 communicates with and extends from the explosion proof gas outlet fitting 84 of the combustion chamber assembly through the explosion proof housing 46 terminating at a point a safe distance from the explosion proof housing 46. The conduit 196 includes a restrictive orifice 198 therein to provide suitable back pressure to gases flowing therethrough from the combustion chamber assembly 48. Again, it will be understood that the conduit 196 is provided with a suitable explosion proof fitting at its point of exit through the explosion proof housing 46. A conduit 200 communicates between the conduit 196 adjacent to the explosion proof housing 46 and the visual indicator 34 of the control unit and panel assembly 12.

Within the explosion proof housing 46 it will be seen that, when switch 24 is "on", electric current, preferably positive 12 volts d.c., is provided to the electronic ignition trigger oscillator 52, the capacitor discharge ignition power unit and coil assembly 50, the solenoid of solenoid valve 58, one terminal of the temperature responsive snap action switch 90, and one terminal of the temperature responsive electrical switch 54. The second terminal of the temperature responsive switch 90 is electrically connected to the solenoids of the solenoid valves 56 and 60. The second terminal of the temperature responsive switch 54 is electrically connected to the solenoid of solenoid valve 62. High tension lead 128 interconnects the spark plug 86 and the coil of the capacitor discharge ignition power unit and coil assembly 50 as noted above in the discussion of FIG. 4. The oscillator 52 is electrically connected to the capacitor discharge ignition power unit and coil assembly 50 by means of the green wire also discussed above in the description of the circuitry illustrated in FIG. 4.

OPERATION

To operate the apparatus 10, the valve 132 of the container assembly 16 is opened to provide non-combustion-supporting gas, such as $CO_2$, to the pressure regulator 130 which, in turn, provides gas at approximately 100 p.s.i. to the apparatus 10. The valve 38 of the control unit and panel assembly 12 is adjusted manually until a suitable background rate of flow of gas is achieved through the gas flow meter 28 to the closed blender tub assembly 20 to prevent the accumulation of explosive flammable gas mixtures in the blender tub assembly 20 under ordinary or usual operating conditions.

Switch 24 is then placed in the "on" position providing electrical current, preferably positive 12 volts d.c., to the capacitor discharge ignition power unit and coil assembly 50, the electronic ignition trigger oscillator assembly 52, the solenoid 58, and the open temperature responsive switches 90 and 54. The pump 162 is also actuated to provide pressurized air to the apparatus 10 via filter 164 and the conduits 166 and 168.

When switch 24 is closed it will be seen that solenoid valve 58 is actuated to direct pressurized air therethrough and through conduit 178 to air motor 180 thus providing power to the pump 184. The pump 184 draws a sample stream of gas from the closed blender tub assembly 20 through conduit 186 and filters 188 and 190 and propels the gas sample stream through the explosion proof gas outlet fitting 194 and conduit 192 into the combustion chamber assembly 48 via the explosion proof gas inlet fitting 80. The sample gas stream exits from the combustion chamber assembly 48 via the explosive proof gas outlet fitting 84 and travels through conduit 196 and restrictive orifice 198 to some location remote from the apparatus 10. Gas pressure is communicated from the conduit 196 through conduit 200 to the visual indicator 34 when the flow of the sample gas stream is uninterrupted thereby placing a visual green indication in the window of the visual indicator 34 to indicate that the apparatus 10 is sampling gas from the blender tub assembly 20.

When the swtich 24 is closed and the indicator light 26 is lit, it will be seen that electric current from the storage battery 40 is applied to both the electronic ignition trigger oscillator assembly 52 and the capacitor discharge ignition power unit and coil assembly 50. The oscillator 52 causes the relay 120 to place the terminal 124 in electrical connection with terminal 122 and ground at a rate of 15 switch closures per second as a result of the 15 Hz oscillation frequency of the oscillator 52. The grounding of the terminal 124 and the green wire from the capacitor discharge power unit attached thereto triggers the capacitor discharge ignition power unit and coil assembly 50 at the rate of 15 discharges per second thereby causing the spark plug 86 to provide a series of high intensity impulses or sparks of approximately 27,000 volts in the interior of the combustion chamber assembly 48 at the frequency of 15 Hz. Experimentation has shown that an ignition frequency of 15 Hz. is optimum in the particular application of the apparatus 10 to provide satisfactory reliable ignition of explosive samples in the combustion chamber assembly 48.

In the event the stream of sample gas from the blender tub assembly 20 passing through the combustion chamber assembly 48 is explosive, the high intensity of ignition discharges from the spark plug 86 will cause the gas sample within the combustion chamber 48 to ignite at which time a significant temperature increase will be experienced within the combustion chamber assembly 48. When the temperature in the combustion chamber assembly 48 rises to 300° F., the temperature responsive snap action switch 90 closes thus providing positive d.c. current to the solenoids of solenoid valves 56 and 60.

When solenoid valve 56 is actuated, $CO_2$ or other suitable non-combustion-supporting gas, is conducted through the valve 56, conduit 146, valve 148, the gas flow meter 28, conduit 150 and gas distribution nozzle 152 into the closed blender tub assembly 20 above the fracturing fluid contained therein. The rate of flow of $CO_2$ through the throttle or needle valve 148 may be adjusted by manipulating the valve 148 and viewing the flow rate indicated on the gas flow meter 28. Once a satisfactory supplementary or booster gas flow rate is achieved, further adjustment of the valve 148 is unnecessary.

When the solenoid valve 60 is actuated, pressurized air from the pump 162 is prevented from passing therethrough and the visual indicator 36 and conduits 172 and 174 are vented to the atmosphere thereby causing the visual indicator 36 to change from black indication to a red indication in the window thereof. It will also be seen that the actuation of the solenoid valve 60 prevents compressed air from passing therethrough to the air motor 180 thus stopping the operation of the air motor and the pump 184 of the gas sample pump assembly 18 which, in turn, temporarily terminates the introduction of gas sample into the combustion chamber assembly 48 thereby allowing the sample within the combustion chamber assembly 48 to be completely consumed and permitting the temperature to decrease within the combustion chamber assembly 48.

When the temperature within the combustion chamber assembly 48 decreases below 300° F. and the temperature responsive snap action switch 90 also cools to a temperature below 300° F. after a suitable time delay, the switch 90 opens and the solenoid valves 56 and 60 are deactivated and allowed to return to their initial positions. When the valves 56 and 60 assume their initial positions, the visual indicator 36 will again show a black indication in the window thereof and the air motor 180 will resume operation driving the pump 184 and again providing a sample gas stream from the closed blender tub assembly 20 to the interior of the combustion chamber assembly 48. It will also be noted that the supplementary supply of non-combustion-supporting gas being provided through the nozzle 152 to the interior of the blender tub assembly 20 will also be shut off. However, it should be kept in mind that the constant background supply of non-combustion-supporting gas controlled by the adjustable throttle valve 38 will continue to be introduced through the nozzle 152 into the blender tub assembly 20.

If, upon a continuation of pumping the sample gas stream into the interior of the combustion chamber assembly 48, ignition of the sample is again experienced, the previously described procedure will be repeated. If it is found that the apparatus 10 is cycling regularly upon the detection of explosive flammable gas mixtures in the combustion chamber assembly 48, the operator may then adjust the throttle valve 38 to increase the constant background flow of non-combustion-supporting gas to the blender tub assembly 20 until the cycling ceases. The time delay characteristics of the switch 90 reduces the cycling frequency under these circumstances providing operational stability.

In the event of some unforeseen malfunction within the explosion proof housing 46 causing an excessive elevation of temperature therein, the temperature responsive electrical switch 54 will close upon the sensing of such a predetermined excessive temperature thereby providing d.c. current to the solenoid of the solenoid valve 62 to actuate the valve. When the solenoid valve 62 is actuated, it will be seen that pressurized air will be conducted therethrough from the pump 162 via conduit 168 to the visual indicator 32 via conduit 170 thus causing the visual indicator 32 to change from a black indication to a red indication in the window thereof indicating an overheating condition. Upon the indication of an overheating condition in the visual indicator 32, the operator may shut down the apparatus 10 by operating the switch 24 to open the circuit between the storage battery 40 and the remainder of the apparatus 10. If desired, the apparatus 10 may be modified to provide automatic shut-down in the event an overheating condition is sensed within the explosion proof housing 46, however, the present apparatus provides the operator with the option of continuing the sampling process so that mere temporary overheating conditions will not automatically shut down the operation of the apparatus 10.

It will also be noted that if desired, an adjustable throttle valve 202 may be interposed in the conduit 178 between the solenoid valve 58 and the air motor 180 to provide adjustment of the operating speed of the air motor 180 and the pump 184. As an alternative, a fixed restrictive orifice may be substituted for the adjustable throttle valve 202 when the adjustment capability is deemed unnecessary.

It will be seen that the apparatus described above and its method of employment provide simple reliable means for constantly monitoring and controlling the composition of flammable gas mixtures in a closed container to prevent the accumulation of explosive gas mixtures therein. The apparatus 10 provides the capability of testing virtually any flammable gas regardless of its composition thus eliminating the calibration difficulties inherent in the utilization of catalytic reaction, gas absorption and spectrum analysis type gas sensors which require specific knowledge of the composition of the gas being sensed and prior calibration therefor.

Changes may be made in the combination and arrangement of parts or elements as set forth in the specification and shown in the drawings without departing from the spirit and scope of the invention as defined in the following claims.

What is claimed is:

1. An apparatus for use with a source of electric current for monitoring and controlling the composition of gaseous mixtures in a substantially closed container to prevent the accumulation of explosive gas mixtures therein, comprising;
   a combustion chamber having an inlet and an outlet;
   conduit means communicating between said closed container and the inlet of said combustion chamber for conveying a sample stream of gaseous mixture from said container to said combustion chamber;
   pump means communicating with said conduit means for propelling the sample gaseous mixture stream through said conduit means to said combustion chamber;
   ignition generation means connected with said source of electric current and communicating with the interior of said combustion chamber for providing periodic ignition impulses to the interior of said combustion chamber to ignite any explosive gas mixture therein;
   temperature responsive switch means communicating with the interior of the combustion chamber and connected to said source of electric current for regulating passage of electric current therethrough in response to temperatures sensed in said combustion chamber; and
   means electrically connected to said temperature responsive switch means and responsive thereto for introducing non-combustion-supporting gas into the enclosed container upon the sensing of a temperature within said combustion chamber greater than a predetermined value.

2. The apparatus as defined in claim 1 wherein said combustion chamber is characterized further to include:
   first and second flame arrestor means positioned respectively in communication with the inlet and outlet of said combustion chamber for preventing the passage of flame from the combustion chamber through the inlet and outlet thereof.

3. The apparatus as defined in claim 1 wherein said means electrically connected to said temperature responsive switch is characterized further to include:
   means connected to said pump means for automatically halting the operation of said pump means upon the sensing of a temperature within said combustion chamber greater than the predetermined value, and, alternately, automatically restarting the operation of said pump means upon sensing a temperature within said combustion chamber less than the predetermined value.

4. The apparatus as defined in claim 1 characterized further to include:
   means for introducing a constant stream of non-combustion-supporting gas into the closed container for preventing the accumulation of explosive gas mixtures therein under ordinary operating conditions.

5. The apparatus as defined in claim 1 wherein said temperature responsive switch means is characterized further to include:
   time delay means formed thereon for retaining said switch means in a closed position passing electric current therethrough for a predetermined time after the temperature sensed in said combustion chamber falls to a value less than the predetermined value causing the switch to initially pass electric current therethrough.

6. The apparatus as defined in claim 1, characterized further to include:
second temperature responsive switch means positioned adjacent to the exterior of said combustion chamber and connected to said source of electric current for regulating passage of electric current therethrough in response to temperatures sensed on the exterior of said combustion chamber;
shut-off means connected to said second temperature responsive switch means for halting operation of said pump means when the temperature adjacent to the exterior of said combustion chamber is greater than a predetermined value.

7. The apparatus as defined in claim 6, wherein:
said shut-off means includes means for automatically halting operation of said pump means when the temperature adjacent to the exterior of said combustion chamber is greater than said predetermined value and override means for selectively overriding said shutoff means and continuing operation of said pump means when the temperature adjacent to the exterior of said combustion chamber is greater than said predetermined value.

8. The apparatus as defined in claim 1 characterized further to include:
thermal insulator means, between a wall of said combustion chamber and said temperature responsive switch means, for minimizing the effect of the temperature of said wall upon said temperature responsive switch means.

9. The apparatus as defined in claim 8 characterized further to include:
second indicator means communicating with the outlet of said combustion chamber for providing visual indication when a sampled stream of gas mixture is being exhausted from said combustion chamber.

\* \* \* \* \*